United States Patent [19]

Boyan et al.

[11] Patent Number: 6,001,352
[45] Date of Patent: Dec. 14, 1999

[54] RESURFACING CARTILAGE DEFECTS WITH CHONDROCYTES PROLIFERATED WITHOUT DIFFERENTIATION USING PLATELET-DERIVED GROWTH FACTOR

[75] Inventors: Barbara D. Boyan, San Antonio, Tex.; Zvi Schwartz, Jerusalem, Israel

[73] Assignee: OsteoBiologics, Inc., San Antonio, Tex.

[21] Appl. No.: 08/829,308

[22] Filed: Mar. 31, 1997

[51] Int. Cl.$^6$ .......................... A61K 35/32; C12N 11/08; C12N 5/00; C12N 5/08

[52] U.S. Cl. .......................... 424/93.7; 424/423; 424/426; 424/548; 435/177; 435/180; 435/325; 435/366; 435/375; 435/377; 435/384; 435/395; 435/396; 435/405

[58] Field of Search .................................. 424/93.7, 85.1, 424/423, 426, 548; 435/177, 180, 182, 384, 395, 405, 325, 366, 375, 377, 396

[56] References Cited

U.S. PATENT DOCUMENTS 5,041,138   8/1991   Vacanti et al. ............................ 623/16
5,786,217   7/1998   Tubo et al. ............................. 435/402

OTHER PUBLICATIONS

Kieswetter, K. et al., "Chondrocyte Regulation by Platelet–Derived Growth Factor–BB in Insulin–like Growth Factor In vitro," *J. Dent. Res.* 74 (IADR Abstract #636), p. 480, 1995.

Kieswetter, K. et al., "Platelet–Derived Growth Factor and Insulin–like Growth Factor–1 Modulate Complementary Aspects of chondrocyte Proliferation, Differentiation, and Protein Synthesis," *Transactions of the Orthopaedic Res. Soc.*, p. 307, 1996.

Antoniades, H.N. and Owen, A.J., "Growth Factors and Regulation of Cell Growth," (1982) *Ann. Rev. Med.* 33:445–463.

Boyan, B.D. et al., "The Effects of Vitamin D Metabolites on the Plasma and Matrix Vesicle Membranes of Growth and Resting Cartilage Cells in Vitro," (1988) *Endrocrinology* 122:2851–2860.

Boyan, B.D. et al., "Differential Expression of Phenotype by Resting Zone and Growth Region Costochondral Chondrocytes In Vitro," (1988) *Bone* 9:185–194.

Boyan, B.D., et al., "In Vitro Studies on the Regulation of Endochondral Ossification by Vitamin D," (1992) *Crit. Rev. Oral Biol. Med.* 3(1/2):15–30.

Bretaudiere, J.P. and Spillman, T., "Alkaline Phosphatases, Routine Method," (1984) In: *Methods of Enzymatic Analysis*, edited by H.U. Bergmeyer (Verlag Chemica, Weinheim) 4:75–92.

Canalis, E. and Lian, J.B., Effects of Bone Associated Growth Factors on DNA, Collagen and Osteocalcin Synthesis in Cultured Fetal Rat Calvariae, (1988) *Bone* 9:243–246.

Centrella, M. et al., "Skeletal tissue and transforming growth factor β," (1988), *FASEB J.* 2:3066–3073.

Centrella, M. et al., "Platelet–Derived Growth Factor Enhances Deoxyribonucleic Acid and Collagen Synthesis in Osteoblast–Enriched Cultures from Fetal Rat Parietal Bone," (1989) *Endocrinology* 125:13–19.

Chen, P. et al., "Chick Limb Bud Mesodermal Cell Chondrogenesis: Inhibition by Isoforms of Platelet–Derived Growth Factor and Reversal by Recombinant Bone Morphogenetic Protein," (1992) *Exp. Cell. Res.* 200:110–117.

Coughlin, S.R. et al., "Platelet–dependent stimulation of porstacyclin synthesis by platelet–derived growth factor," (1980) *Nature* 288:600–602.

Crabb, I.D. et al., "Synergistic Effect of Transforming Growth Factor β and Fibroblast Growth Factor on DNA Synthesis in Chick Growth Plate Chondrocytes," (1990) *J. Bone Miner. Res.* 5:1105–1112.

Demarquay, D. et al., "Stimulation of GH of IGF1 Proforms Synthesized by Rabbit Chondrocytes Cultured with bFGF in Serum–Free Medium," (1992) *Experiment Cell. Res.* 202:412–422.

Fujisato, T. et al., "Effect of basic fibroblast growth factor on cartilage regeneration in chondrocyte–seeded collagen sponge scaffold," (1996) *Biomaterials* 17:155–162.

Hale, L.V. et al., "Effect of Vitamin D Metabolites on the Expression of Alkaline Phosphatase Activity by Epiphyseal Hypertrophic Chondrocytes in Primary Cell Culture," (1986) *J. Bone Miner. Res.* 1:489–495.

Hauschka, P.V. et al., "Growth Factors in Bone Matrix," (1986) *J. Biol. chem.* 261:12665–12674.

Heldin, C.H. et al., "Structural and functional aspects of platelet–derived growth factor," (1988) *British J. Cancer* 57:591–593.

Hock, J.M. et al., "Insulin–Like Growth Factor I Has Independent Effects on Bone Matrix Formation and Cell Replication," (1988) *Endocrinology* 122:254–260.

Hock, J.M. and Canalis, E., "Platelet–Derived Growth Factor Enhances Bone Cell Replication, but not Differentiated Function of Osteoblasts," (1994) *Endocrinology* 134:1423–1428.

Kato, Y. and Iwamoto, M., "Fibroblast Growth Factor Is an Inhibitor of Chondrocyte Terminal Differentiation," (1990) *J. Biol. Chem.* 265:5903–5909.

(List continued on next page.)

*Primary Examiner*—David M. Naff
*Attorney, Agent, or Firm*—Greenlee, Winner and Sullivan

[57] ABSTRACT

A method for stimulating chondrocyte proliferation and inhibiting chondrocyte differentiation along the endochondral developmental pathway is provided comprising contacting condrocytes with an effective amount of Platelet-Derived Growth Factor (PDGF) such as PDGF-BB, PDGF-AA OR PDGF-AB in the substantial absence of growth factors which promote cell differentiation. This allows such cells to be multiplied in culture for loading onto a scaffolding material and implanting into a cartilage or bone wound.

2 Claims, 10 Drawing Sheets

OTHER PUBLICATIONS

Kinoshita, A. et al., "Demonstration of Receptors for Epidermal Growth Factor on Cultured Rabbit Chondrocytes and Regulation of Their Expression by Various Growth and Differentiation Factors," (1992) *Biochem. Biophys. Res. Comm.* 183:14–20.

O'Keefe, R.J. et al., "Effects of Transforming Growth Factor–β on Matrix Synthesis by Chick Growth Plate Chondrocytes," (1988) *Endocrinology* 122:2953–2961.

O'Keefe, R.J. et al., "Countercurrent Centrifugal Elutriation," (1989) *J. Bone Joint Surg.* 71A:607–620.

Peterkofsky, B. and Diegelmann, R., "Use of a Mixture of Proteinase–Free Collagenases for the Specific Assay of Radioactive Collagen in the Presence of Other Proteins," (1971) *Biochemistry* 10:988–994.

Pfeilschifter, J. et al., "Stimulation of Bone Matrix Apposition in Vitro by Local Growth Factors: A Comparison between Insulin–like Growth Factor I, Platelet–Derived Growth Factor, and Transforming Growth Factor β," (1990) *Endocrinology* 127:69–75.

Raisz, L.G. et al., "Comparison of the Effects of a Potent Synthetic Analog of Bovine Parathyroid Hormone With Native bPTH–(1–84) and Synthetic bPTH0–(1–34) on Bone Resorption and Collagen Synthesis," (1979) *Calcif. Tissue Int.* 29:215–218.

Ross, R. et al., "The Biology of Platelet–Derived Growth Factor," (1986) *Cell* 46:155–169.

Schwartz, Z. and Boyan, B.D., "The Effects of Vitamin D Metabolites on Phospholipase $A_2$ Activity of Growth Zone and Resting Zone Cartilage Cells in Vitro," (1988) *Endocrinology* 122:2191–2198.

Schwartz, Z. et al., "Effects of Vitamin D Metabolites on Collagen Production and Cell Proliferation of Growth Zone and Resting Zone Cartilage Cells in Vitro," (1989) *J. Bone Miner. Res.* 4:199–207.

Schwartz, Z. et al., "Direct Effects of Transforming Growth Factor–β on Chondrocytes Are Modulated by Vitamin D Metabolites in a Cell Maturation–Specific Manner," (1993) *Endocrinology* 132:1544–1552.

Schwartz, Z. et al., "Treatment of Resting Zone Chondrocytes with 24,25–Dihydroxyvitamin $D_3$ [24,25–$(OH)_2D_3$] Induces Differentiation into a 1,25–$(OH)_2D_3$–Responsive Phenotype Characteristic of Growth Zone Chondrocytes," (1995) *Endocrinology* 136:402–411.

Schwartz, Z. et al., "Dexamethasone promotes von kossa–positive nodule formation and increased alkaline phosphatase activity in costochondral chondrocyte cultures," (1995) *Endocrine* 3:351–360.

Skoog, V. et al., "The Effect of Growth Factors and Cynovial Fluid on Chondrogenesis in Perichondrium," (1990) *Scand J. Plast. Reconstr. Hand Surg.* 24:89–95.

Stiles, C.D., "The Molecular Biology of Platelet–Derived Growth Factor," (1983) *Cell* 33:653–655.

Sunic, D., et al., "Insulin–like growth factor binding proteins (IGF–BPs) in bovine articular and ovine growth–plate chondrocyte cultures: their regulation by IGFs and modulation of proteoglycan synthesis," (1995) *Biochim. Biophys. Acta* 1245:43–48.

Tsukamoto, T. et al., "Platelet–Derived Growth Factor B Chain Homodimer Enhances Chemotaxis and DNA Synthesis in Normal Osteoblast–like Cells," (1991) *Biochem. Biophys. Res. Comm.* 175:745–751.

Wang, J.S. and Aspenberg, P., "Basic fibroblast growth factor and bone induction in rats," (1993) *Acta Orthopaedica Scand.* 64:557–561.

Wroblewski, J. and Edwall–Arvidsson, C., "Inhibitory Effects of Basic Fibroblast Growth Factor on Chrondocyte Differentiation," (1995) *J. Bone Miner. Res.* 10:735–742.

Wuthier, R.E. and Register, T.C., "Role of Alkaline Phosphatase, a Polyfunctional Enzyme, in Mineralizing Tissues," (1985) In: *Chemistry and Biology of Mineralized Tissues*, Butler, W.T. (ed), EBSCO Media, Birmingham, Alabama, pp. 113–124.

Zhang, L. et al., "Human osteoblasts synthesize and respond to platelet–derived growth factor," (1991) *Am. J. Physiol.* 261:C348–C354.

Lynch, S.E. et al., "The combination of platelet–derived growth factor–BB and insulin–like growth factor–I stimulates bone repair in adult Yucatan miniature pigs," (1994) *Wound Rep. Reg.* 2:182–190.

RESURFACING CARTILAGE DEFECTS WITH CHONDROCYTES PROLIFERATED WITHOUT DIFFERENTIATION USING PLATELET-DERIVED GROWTH FACTOR

BACKGROUND OF THE INVENTION

Chondrocytes are mesenchymal cells that have a characteristic phenotype based primarily on the type of extracellular matrix they produce. The precursor cells produce type I collagen but when they become committed to the chondrocyte lineage, they synthesize type II collagen. In addition, committed chondrocytes produce proteoglycan aggregate, called aggrecan, which has glycosaminoglycans that are highly sulfated.

For most cartilaginous tissues, chondrocytes are relatively sparsely distributed in the extracellular matrix; mitosis occurs, but at a low rate; and in part because the tissue is essentially not vascularized, the tissue remains stable over time. A consequence of this is that when damage does occur, it repairs slowly, if at all.

Where cartilage interfaces with bone, the chondrocytes continue to mature along the endochondral pathway. Eventually they hypertrophy, degrade the proteoglycan aggregate, and calcify their matrix. This occurs at different rates, depending on the tissue site, the age of the animal, and the presence of disease or abnormal distribution of force.

The region at the interface of articular cartilage and subchondral bone is called the tidemark. During aging the cartilage becomes thinner as the tidemark continues to form. In osteoarthritis this is speeded up. In the growth plate, long bones increase in length via increased proliferation of the chondrocytes but after proliferation occurs, the cells enter into the hypertrophic stage of differentiation. In fracture repair and bone induction in response to demineralized bone graft or bone morphogenetic protein (BMP), the transition occurs more quickly.

Most of the growth factors being examined for use in cartilage and bone were identified because they increased bone formation, either by increasing endochondral differentiation or by acting on osteoblasts directly. These growth factors have multiple effects. They promote differentiation of mesenchymal cells. For example, transforming growth factor β(TGFβ) can induce mesenchymal cells to become cartilage cells in vitro or in vivo. BMP induces mesenchymal cells to become chondrocytes in vivo in mesenchymal tissues that would not normally support bone or cartilage formation. In bone, BMP causes the mesenchymal cells to become chondrocytes when oxygen tension is low or to become osteoblasts when oxygen tension is high.

Growth factors can also cause already-committed cells to differentiate further along their lineage. Factors like insulin-like growth factor (IGF's) or basic fibroblast growth factor (bFGF) do not affect differentiation of mesenchymal cells into cartilage or bone cells in vitro, but in vivo, they enhance the expression of a mature calcifying chondrocyte or osteoblast. TGFβ and BMPs also have effects on already-committed cells. All four of these factors cause resting zone chondrocytes to acquire a phenotype typical of hypertrophic cells. Thus, they will eventually calcify their matrix, supporting endochondral bone formation. If the goal is to enhance bone formation, this is good. But if the goal is to get stable, non-calcified cartilage, this outcome is exactly the opposite of what is desired.

It is an object of this invention, to provide a method to aid in the healing of cartilage wounds by enhancing chondrocyte production without causing further differentiation along the endochondral developmental pathway resulting in calcified cartilage.

Temporally, the release of PDGF from platelets is one of the initial events that occurs in the resolution of a wound. PDGF appears to enhance cartilage and bone formation (Lynch et al., 1994), but it has not previously been known whether this is due to an increase in the pool of less mature cells, or to a direct effect on the differentiation of those cells. PDGF is well known as a competence growth factor (Antoniades et al., 1982; Tsukamoto et al., 1991) and has been shown to initiate extensive proliferation of osteoblasts (Centrella et al., 1989; Hock et al., 1988).

Previous studies also have shown that PDGF regulates extracellular matrix synthesis by osteoblasts in addition to its effects on proliferation. The precise effect of PDGF on matrix synthesis is not clear, with some studies reporting an inhibition of collagen production (Canalis and Lian, 1988), and others reporting no change (Centrella et al. 1989).

Considerable similarities exist between the events that occur in endochondral bone development and those that occur during wound healing in bone. These processes involve the induction of mesenchymal cells into and along the chondrocyte lineage by chondrogenic growth factors like transforming growth factor beta (TGFβ) (Centrella et al., 1988; Crabb et al., 1990; Schwartz et al., 1993), insulin-like growth factor (IGF) (Demarquay et al., 1992; Sunic et al., 1995; Wroblewski et al., 1995), and basic fibroblast growth factor (bFGF) (Fujisato et al., 1996; Kato et al., 1990; Wang et al., 1993).

In bone wound healing in vivo, enhanced proliferation of osteochondroprogenitor cells is an important first step. Platelet-derived growth factor (PDGF), a cytokine which stimulates proliferation of mesenchymal cells in a broad range of tissues (Antoniades et al., 1982 ; Heldin et al., 1988; Ross et al., 1986; Stiles, 1983), is released from platelets at wound sites (Coughlin et al., 1980). In addition, PDGF is produced by osteoblasts (Zhang et al., 1991) and stored in bone (Hauschka et al., 1986), further increasing its local concentration, and as a result, increasing the pool of osteochondroprogenitor cells.

PDGF is a disulfide-linked dimer with a molecular weight of approximately 25 kDa (Coughlin et al., 1980). PDGF-BB is one of three isoforms of PDGF resulting from the dimeric combination of two distinct, but structurally related, polypeptide chains designated as A and B. Fibroblasts, smooth muscle cells, periodontal ligament cells, and osteoblastic cells have all been shown to respond to this cytokine (Centrella et al., 1989, Kinoshita et al., 1992; Pfeilschifter et al., 1990; Tsukamoto et al., 1991). In addition to its stimulatory effect on osteoblast proliferation (Centrela et al., 1989; Canalis and Lian, 1988; Hock et al., 1994), other aspects of cell metabolism and phenotypic expression are affected as well.

Studies examining matrix production and differentiation markers have suggested that exposure of fetal rat calvarial cells to PDGF has an inhibitory effect on collagen synthesis and no effect on osteocalcin production (Canalis et al., 1998). Other studies by the same group on cells isolated from fetal rat parietal bone, while showing enhanced rates of increased collagenase-digestible and noncollagenase-digestible protein production, demonstrated no difference in the overall relative collagen synthesis (Centrella et al., 1989). These observations suggest that PDGF has an overall anabolic effect on the cells, but does not promote osteoblastic differentiation.

To date, attention to the effects of PDGF, particularly the BB isoform, on chondrocytes has been relatively limited. In vitro studies by Chen et al. (Chen et al., 1992) appear to indicate that chick limb bud mesodermal chondrogenesis is inhibited by PDGF. Others, however, have observed chondrogenic differentiation when cultures of perichondrial cells were stimulated with PDGF (Skoog et al., 1990).

It is also an object of this invention to teach how PDGF may be used to enhance proliferation, control matrix synthesis, and inhibit endochondral maturation of chondrocytes, cells whose regulation is essential to development of cartilage and endochondral bone.

Publications referred to herein are listed below. All publications referred to herein are hereby incorporated by reference.

Antoniades, H. N. and Owen, A. J. (1982) *Ann. Rev. Med.* 33:445–463.

Boyan, B. D. et al. (1988 *a*) *Endocrinology* 122:2851–2860.

Boyan, B. D. et al. (1988 *b*) *Bone* 9:185–194.

Boyan, B. D. et al. (1992) *Crit. Rev. Oral Biol. Med.* 3(1/2):15–30.

Bretaudiere, J. P. and Spillman, T. (1984) *In: Methods of Enzymatic Analysis*, edited by H. U. Bergmeyer (Verlag Cbemica, Weinheim) 4:75–92.

Canalis, E. and Lian, J. B. (1988) *Bone* 9:243–246.

Centrella, M. et al (1988) *FASEB J.* 2:3066–3073.

Centrella, M. et al. (1989) *Endocrinology* 125:13–19.

Chen, P. et al (1992) *Exp. Cell. Res.* 200:110–117.

Coughlin, S. R. et al. (1980) *Nature* 288:600–602.

Crabb, I. D. et al (1990) *J. Bone Miner. Res.* 5:1105–1112.

Demarquay, D. et al. (1992) *Experiment Cell. Res.* 202:412–422.

Fujisato, T. et al. (1996) *Biomaterials* 17:155–162.

Hale, L. V. et al. (1986) *J. Bone Miner. Res.* 1:489–495.

Hauschka, P. V. et al. (1986) *J. Biol. chem.* 261:12665–12674.

Heldin, C. H. et al. (1988) *British J. Cancer* 57:591–593.

Hock, J. M. et al. (1988) *Endocrinology* 122:254–260.

Hock, J. M. and Canalis, E. (1994) *Endocrinology* 134:1423–1428.

Kato, Y. and Iwamoto, M. (1990) *J. Biol. Chem.* 265:5903–5909.

Kinoshita, A. et al. (1992) *Biochem. Biophys. Res. Comm.* 183:14–20.

Lynch, S. E. et al. (1994) *Wound Repair Regen.* 2:182–190.

O'Keefe, R. J. et al. (1988) *Endocrinology* 122:2953–2961.

O'Keefe, R. J. et al. (1989) *J. Bone Joint Surg.* 71A:607–620.

Peterkofsky, B. and Diegelmann, R. (1971) *Biochemistry* 10:988–994.

Pfeilschifter, J. et al. (1990) *Endocrinology* 127:69–75.

Raisz, L. G. et al. (1979) *Calcif. Tissue Int.* 29:215–218.

Ross, R. et al. (1986) *Cell* 46:155–169.

Schwartz, Z. and Boyan, B. D. (1988) *Endocrinology* 122:2191–2198.

Schwartz, Z. et al. (1989) *J. Bone Miner. Res.* 4:199–207.

Schwartz, Z. et al. (1993) *Endocrinology* 132:1544–1552.

Schwartz, Z. et al. (1995 *a*) *Endocrinology* 136:402–411.

Schwartz, Z. et al. (1995 *b*) *Endocrine* 3:351–360.

Skoog, V. et al. (1990) *Scand. J. Plast. Reconstr. Hand Surg.* 24:89–95.

Stiles, C. D. (1983) *Cell* 33:653–655.

Sunic, D. et al. (1995) *Biochim. Biophys. Acta* 1245:43–48.

Tsukamoto, T. et al. (1991) *Biochem. Biophys. Res. Comm.* 175:745–751.

Wang, J. S. and Aspenberg, P. (1993) *Acta Orthopaedica Scand.* 64:557–561.

Wroblewski, J. and Edwall-Arvidsson, C. (1995) *J. Bone Miner. Res.* 10:735–742.

Wuthier, R. E. and Register, T. C. (1985) *In: Chemistry and Biology of Mineralized Tissues,* Butler, W. T. (ed), EBSCO Media, Birmingham, Alabama, pp. 113–124.

Zhang, L. et al. (1991) *Am. J. Physiol.* 261:C348–C354.

SUMMARY OF THE INVENTION

This invention provides a method for causing committed cartilage cells to proliferate and, at the same time, to retain their chondrogenic phenotype as evidenced by sulfated glycosaminoglycan production. These cells do not progress to a hypertrophic phenotype based on the fact that alkaline phosphatase does not increase nor do the cells become responsive to $1,25-(OH)_2D_3$, both of which are hallmarks of hypertrophic cells. Cell maturation along the endochondral pathway is not enhanced, and preferably is inhibited.

Chondrogenesis, or the process of forming cartilage, involves the commitment of pluripotential mesenchymal cells to the chondrocyte lineage and their differentiation along this pathway. This process requires the cells to produce and respond to a number of cytokines and growth factors, including platelet derived growth factor (PDGF), insulin like growth factor (IGF), basic fibroblast growth factor (bFGF), transforming growth factor beta (TGFβ), bone morphogenetic protein (BMP), and cartilage derived growth factor (CDGF). Once the cells enter the chondrocyte lineage, they produce and maintain a matrix rich in collagen type II and proteoglycan aggregate. Chondrocytes that are found in articular cartilage synthesize and maintain this matrix over long periods of time. At the base of the articular cartilage, where it interfaces with subchondral bone, there is a small region of cells that continue to differentiate forming calcified cartilage. This region is called the tidemark and is similar in many ways to the growth plate cartilage of long bones.

When condrocytes enter into the endochondral developmental pathway, they undergo hypertrophy, requiring extensive remodeling of their extracellular matrix. These cells make extracellular matrix vesicles which contain metalloproteinases to degrade the large proteoglycan aggregate. The matrix vesicles also contain enzymes involved in calcification. Eventually calcium phosphate crystals form within the matrix vesicles and finally along the collagen fibrils in the matrix. At the base of the growth plate the matrix becomes calcified and the cells make a number of proteins associated with calcified bone. Ultimately, the calcified cartilage becomes vascularized and osteogenic cells begin to form bone.

When attempting to resurface articular cartilage it is necessary to enable mesenchymal cells to enter the chondrocyte lineage but it is counterproductive to permit them to traverse through the entire differentiation cascade because bone will form if the cartilage becomes calcified. Unfortunately, most of the factors which promote chondrogenesis cause the cells to enter the endochondral lineage. BMP-2 and osteogenic protein 1 (OP-1 or BMP-7) both induce bone formation in vivo by causing mesenchymal cells to differentiate into chondrocytes which traverse the entire endochondral cascade. TGFβ appears to cause mesenchymal cells to become chondrocytes but it is less clear how far along the pathway these cells progress. The situation is further confused by the fact that the cells themselves produce growth factors and cytokines which then have both autocrine and paracrine effects, further promoting differentiation.

Studies using the costochondral cartilage growth plate as a model indicate that the cells in the resting cell zone (also called a reserve cell zone) are similar to hyaline chondrocytes like those in articular cartilage. These cells are surrounded by a proteoglycan rich matrix which is not calcified. In vitro and in vivo, these cells respond primarily to the 24,25-$(OH)_2D_3$ metabolite of vitamin D. In contrast, cells from the prehypertrophic and upper hypertrophic zones of the costochondral cartilage (growth zone cartilage) respond primarily to the 1,25-$(OH)_2D_3$ metabolite. When resting zone cells are exposed to 24,25-$(OH)_2D_3$ for 36 hours or more, they acquire a growth zone chondrocyte phenotype with respect to responsiveness to the vitamin D metabolites. These cells lose responsiveness to 24,25-$(OH)_2D_3$ and become responsive to 1,25-$(OH)_2D_3$.

The two cell types differ in a number of other ways reflecting their differences in maturation state with respect to the chondrocyte lineage. We have examined the short-term and long-term responses of these cells to a number of growth factors including bFGF, BMP-2, TGFβ, 1, IGF-1, and PDGF-BB. The nature of the response is cell maturation dependent, growth factor specific, and time dependent. Interestingly, with the exception of PDGF-BB, all of the growth factors induced a change in the phenotypic expression of the chondrocytes such that resting zone cells become responsive to 1,25-$(OH)_2D_3$. Only PDGF-BB caused resting zone cells to increase in number without stimulating alkaline phosphatase activity, a marker of the endochondral lineage. Moreover, the PDGF-BB treated cells make increased sulfated proteoglycan, the hallmark of a hyaline type chondrocyte.

Since chondrocyte cell therapy for resurfacing of articular cartilage defects requires cell expansion without loss of the hyaline phenotype, treatment of the cells with PDGF, preferably with about 1–150 ng PDGF-BB, for 30 minutes to five days can be a useful method. In the invention, the patient's cartilage is harvested from a non-weight bearing region of the joint to be treated or from costochondral resting zone cartilage. The cells are isolated by enzymatic digestion of the cartilage (preferentially using collagenase in Hank's balanced salt solution), treated with PDGF, preferably with 100 ng/ml recombinant human PDGF-BB (range 1–300 ng/ml) for 30 minutes to 24 hours, preferably two hours, in culture medium, preferably containing about 10% patient's serum (complete medium, preferentially Dulbecco's modified Eagle's medium), rinsed in complete medium to remove any exogenous PDGF, and then loaded onto a suitable scaffold (preferentially a cell scaffold as described in U.S. patent application Ser. No. 08/727,204 and corresponding PCT application PCT/US 96/16049, incorporated herein by reference) prior to placement in the articular cartilage defect. Other growth factors which induce cell differentiation should not be substantially present in the culture medium and should not be added to the medium.

PDGF can also be used in conjunction with other growth factors to enhance cell proliferation together with cell differentiation. For example, pluripotential mesenchymal cells can be induced to enter the chondrogenic pathway with either BMP or TGFβ, while promoting increased cell number with PDGF. Perichondrial cells or mesenchymal stem cells are preferred for this application.

The method for stimulating chondrocyte proliferation and without enhancing chondrocyte differentiation along the endochondral maturation pathway of this invention comprises contacting the chondrocytes with an effective amount of PDGF to measurably enhance chondrocyte proliferation, e. g. , applying to a wound surface a solution containing about 1 to about 300 ng PDGF per ml, or coating and impregnating a biodegradable implant material with said solution to be placed in a bone or cartilage defect, or incorporating PDGF into a biodegradable implant material such as described in U.S. patent application Ser. No. 08/727, 204 filed Oct. 8, 1996, now U.S. Pat. No. 5,863,297, and corresponding PCT application PCT/US 96/16049 incorporated herein by reference, or applying such a solution to a particulate bone graft material or extender. The term "bone graft material" includes both autologous bone graft materials or bone graft substitutes or extenders made of bone materials or synthetic materials, as known to the art. In this way, production of sufficient chondrocytes can be stimulated to provide optimal wound healing before differentiation of the cells occurs.

The term "platelet-derived growth factor" (PDGF) refers to all the isoforms of PDGF, including PDGF-AA, PDGF-BB, and PDGF-AB.

Other growth factors which stimulate chondrocyte cell differentiation should not be substantially present, i. e. , should not be present except to the extent they are naturally produced in the in vivo or in vitro environment in which the method is being practiced.

Cell scaffold materials in addition to those described above are known to the art, and may be made of biodegradable or non-biodegradable materials.

DETAILED DESCRIPTION OF THE PREFERRED EMBODIMENTS

Figure 1:
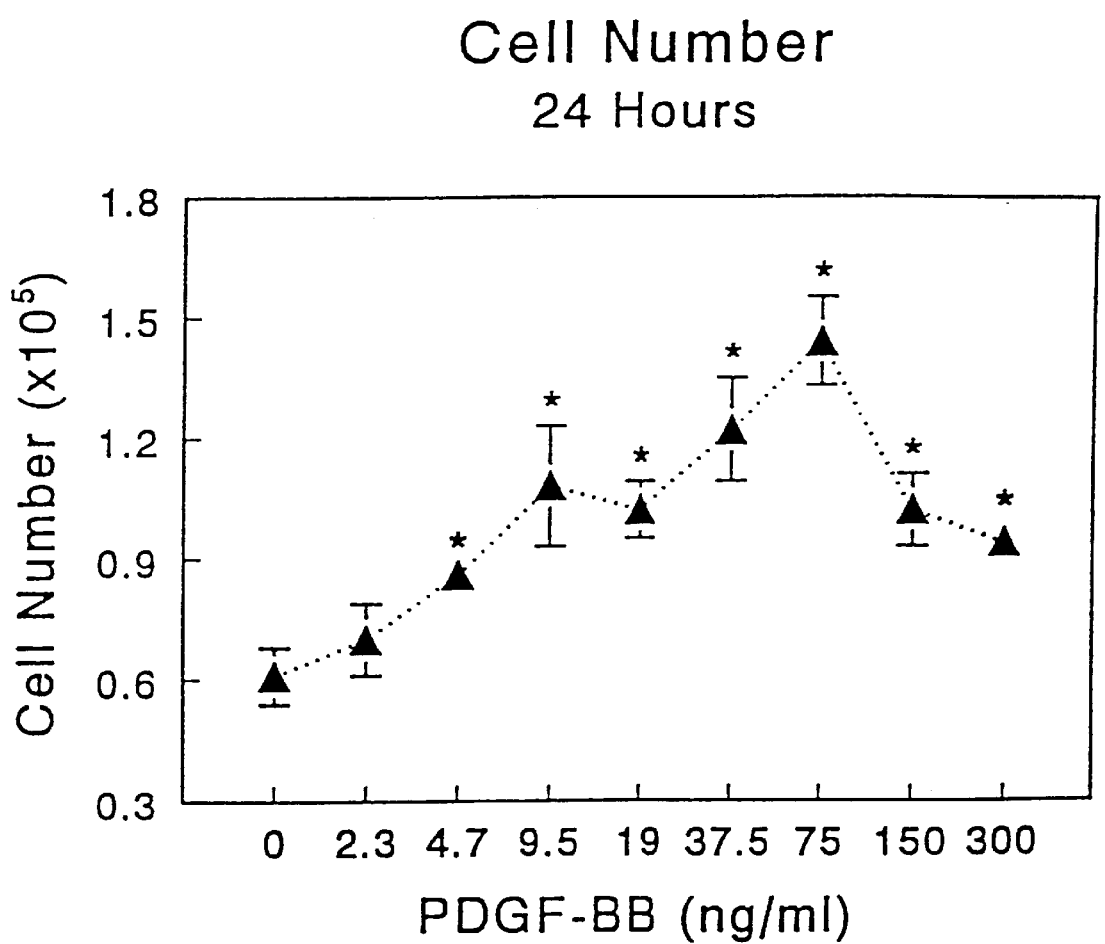
FIG. 1. Number of resting zone chondrocytes after treating confluent cultures for 24 hours with 0–300 ng/ml PDGF-BB. Values are the mean ±SEM of six cultures. *P<0. 05, treatment vs. control. Data are from one of two replicate experiments yielding similar results.

This invention provides a method of using Platelet-Derived Growth Factor (PDGF) to increase cartilage cell number without promoting further differentiation along the endochondral differentiation pathway.

In the studies reported below, which were undertaken to examine the effects of the cytokine PDGF-BB on the proliferation, matrix synthesis and differentiation of chondrocytes, it was shown that PDGF-BB has a direct effect on chondrocytes in the endochondral lineage. The cytokine stimulates cell proliferation and production of a cartilage-specific matrix based on increased sulfate incorporation. In contrast, PDGF-BB inhibits the increase in alkaline phosphatase-specific activity normally seen in post-confluent cultures (Schwartz et al. , 1995b) and does not promote the transition of the cells to a 1,25-(OH)$_2$D$_3$-responsive growth zone phenotype, indicating that the cytokine maintains the cells in a less mature phenotype.

EXAMPLES

[$^3$H]-proline incorporation was used to examine the effect of PDGF-BB on protein synthesis. Neither the amount of collagenase-digestible protein nor the amount of noncollagenase-digestible protein was affected; thus, there was no change in the amount of collagen synthesized. However, sulfate incorporation was markedly enhanced, indicating a specific effect of PDGF on expression of the cartilage phenotype. It is believed that the effect of PDGF on proteins is involved in the sulfation of cartilage glycosaminoglycans.

The increase in [$^{35}$S]-sulfate incorporation in the resting zone cell cultures at 24 hours occurred at all concentrations of PDGF used and was evident after eight days of exposure. Results published by Chen et al. (Chen et al. , 1992) using Stage 24 chick limb bud mesodermal cells differed considerably from those presented here. Exposure of these cells to the various isoforms of PDGF for up to two days resulted in a large decrease in [$^{35}$S]-sulfate incorporation. When the chick limb bud cells were exposed to PDGF for 3–4 days, no differences between treatment and control cultures were noted. These differences may be attributed in part to culture conditions, since the studies conducted by Chen et al. were done under serum-deprived conditions. They may also reflect differences in the maturation stage of the cells, with chick limb bud having a greater proportion of pluripotential osteochondral progenitors and the resting zone cell cultures used in the present study being committed chondrocytes.

While the results of this study indicate that the effect of PDGF on chondrocytes in the early stages of endochondral maturation is to promote proliferation and expression of a matrix typical of a resting zone chondrocyte, they also demonstrate that PDGF inhibits the progression of cells to a more mature growth zone phenotype. Although a 24-hour exposure to PDGF had no effect on alkaline phosphatase-specific activity in confluent cultures of resting zone cells, by 48 hours post-confluence, PDGF decreased alkaline phosphatase-specific activity in the cells to levels typical of confluent cultures. Normally, post-confluent cultures of resting zone and growth zone chondrocytes continue to express increased enzyme activity through 24 days in culture (Schwartz et al. , 1995b). This is associated with the formation of nodules and, ultimately, the appearance of von Kossa-positive deposits within the nodules. The effect of PDGF was most evident in isolated cells in comparison with cell layers at later time points, indicating pre-existing matrix vesicle alkaline phosphatase was not affected by the cytokine.

Not only was the normal increase in alkaline phosphatase specific activity seen in post-confluent cultures (Schwartz et al. , 1995b) inhibited in the present study, but treatment of the cells with PDGF for up to five days failed to elicit a 1,25-(OH)$_2$D$_3$-responsive phenotype in the resting zone chondrocyte cultures. In contrast, treatment with 24,25-(OH)$_2$D$_3$ for 36 hours (Schwartz et al. , 1995a), with TGFβ for 48 hours or with BMP-2 for 72 hours, causes resting zone chondrocytes to respond to 1,25-(OH)$_2$D$_3$ in a manner identical to a growth zone chondrocyte with respect to stimulation of alkaline phosphatase and regulation of cell proliferation, protein synthesis, and proteoglycan sulfation.

The purpose of this study was to examine the effects of PDGF-BB on the proliferation, matrix synthesis, and differentiation of chondrocytes, a cell whose regulation is essential to development of endochondral bone. A well-established cell culture model (Boyan et al. , 1988 b; Schwartz et al. , 1989) was used which permits comparison of chondrocytes at two distinct stages of endochondral maturation: the less mature resting zone chondrocyte and the more terminally differentiated growth zone chondrocyte. The first portion of the study examined cellular response of confluent cultures of resting zone cells exposed to PDGF-BB for 24 hours. The second part of the study examined the ability of PDGF-BB to promote endochondral bone formation by examining the long-term response of the cells to the cytokine and by determining whether resting zone chondrocytes exposed to the growth factor develop a growth zone chondrocyte phenotype, based on responsiveness to 1,25-(OH)$_2$D$_3$.

Confluent cultures of rat costochondral resting zone cartilage cells were incubated with 0–300 ng/ml PDGF-BB for 24 hours to determine whether dose-dependent changes in cell proliferation (cell number and [$^3$H]-thymidine incorporation), alkaline phosphatase specific activity, [$^{35}$S]-sulfate incorporation, or [$^3$H]-proline incorporation into collagenase-digestible or noncollagenase-digestible protein, could be observed. Long-term effects of PDGF were assessed in confluent cultures treated for 1, 2, 4, 6, 8 or 10 days with 37. 5 or 150 ng/ml PDGF-BB. To determine whether PDGF-BB could induce resting zone chondrocytes to change maturation state to a growth zone chondrocyte phenotype, confluent resting zone cell cultures were treated for 1, 2, 3 or 5 days with 37. 5 or 150 ng/ml PDGF-BB and then challenged for an additional 24 hours with $1\alpha,25$-$(OH)_2$ $D_3$. PDGF-BB caused a dose-dependent increase in cell number and [$^3$H]-thymidine incorporation at 24 hours. The proliferative effect of the cytokine decreased with time. PDGF-BB had no effect on alkaline phosphatase at 24 hours but, at later times, the cytokine prevented the normal increase in enzyme activity seen in post-confluent cultures. This effect was primarily on the cells and not on the matrix. PDGF-BB stimulated [$^{35}$S]sulfate incorporation at all times examined but had no effect on [$^3$H]-proline incorporation into either the collagenase-digestible or noncollagenase-digestible protein pools. Thus, percent collagen production was not changed. Treatment of the cells for up to five days with PDGF-BB failed to elicit a 1,25-$(OH)_2D_3$-responsive phenotype of rat costochondral growth zone cartilage cells. These results show that committed chondrocytes respond to PDGF-BB with increased proliferation. The effect of the cytokine is to enhance cartilage matrix production but at the same time to prevent progression of the cells along the endochondral maturation pathway.

Materials and Methods

Cell Culture

Resting zone chondrocytes were isolated from the costochondral cartilage of adult male Sprague-Dawley rats as previously described (Boyan et al. , 1988b). Cells were released from the cartilage by sequential incubation in 0. 25% trypsin (Gibco, Grand Island, N.Y.), and then 0. 02% type II collagenase. Following digestion of the matrix, the cells were plated at a density of 10,000 cells/cm$^2$. Cells were cultured in Dulbecco's modified Eagle's medium (DMEM) containing 10% fetal bovine serum (FBS), 1% antibiotics and 50 μg/ml ascorbic acid in an atmosphere of 100% humidity, 5% $CO_2$, and 37° C. Culture media were changed at 24 hours and thereafter at 48-hour intervals. At confluence, the cells were subcultured and replated at the initial seeding density. Experiments were conducted using fourth passage cells plated at a density of 10,000 cells/cm$^2$. Previous studies have shown that at this passage, the cells retain their cartilage phenotype (Boyan et al. , 1988a, 1988b; Schwartz et al. , 1989) as well as their responsiveness to hormones (Boyan et al. , 1988a, 1988b; Schwartz and Boyan, 1988; Schwartz et al. , 1989, 1995a) and growth factors (Schwartz et al. , 1993).

Lyophilized recombinant human PDGF-BB (R & D Systems, Minneapolis, Minn.) was solubilized in sterile 4 mM HCl containing 0. 1% bovine serum albumin (BSA) at a concentration of 300 μg/ml. The experimental media were prepared by diluting the PDGF-BB stock solution with DMEM containing 10% FBS, 1% antibiotics, and 50μg/ml ascorbic acid. All experiments were conducted on confluent cultures. At confluence, the experimental media were added to the wells. Dose-response studies were conducted at concentrations ranging from 0 to 300 ng/ml. Time course studies were conducted for one to ten days post confluence and the cultures exposed to either 37. 5 or 150 ng/ml PDGF for the entire culture period. Control cultures were exposed to media containing the vehicle. Media were changed every second day.

Cell Proliferation

Cell Number

At harvest, cells were rinsed with DMEM. They were then released from the polystyrene culture surface by the addition of 0. 25% trypsin in Hank's balanced salt solution (HBSS) containing 1 mM ethylene diamine tetraacetic acid (EDTA) for ten minutes at 37° C. The reaction was terminated by the addition of DMEM containing 10% FBS. Cell suspensions were centrifuged at 500×g for ten minutes and the supernatant decanted. The cell pellet was washed with phosphate-buffered saline (PBS) and resuspended in physiologic saline. Cell viability was assessed by trypsin blue exclusion and always found to be greater than 95%. Cell number was determined using a Coulter Counter (Hialeah, Fla.).

[$^3$H]-Thymidine Incorporation

At subconfluence (80% confluency), the cells were placed into quiescence by changing the media from DMEM containing 10% FBS to DMEM containing 1% FBS (Schwartz et al. , 1989). The cells were maintained in the 1% FBS media for 48 hours. At this time they were confluent, and experimental media containing the cytokine and 1% FBS were added. After 20 hours, [$^3$H]-thymidine (1 μCi/ml) in DMEM was added to the wells, resulting in a final isotope concentration of 0. 34 μCi/ml. Following the four-hour incubation, the media were removed, the cells washed twice with PBS, and then twice with 5% trichloroacetic acid (TCA). After the second wash, the cells were treated in TCA for 30 minutes at 4° C. The wells were air-dried after removal of the TCA and incubated overnight in 1% sodium dodecyl sulfate (SDS). Radioactivity was determined by liquid scintillation spectroscopy.

Alkaline Phosphatase Specific Activity

Since it is well known that the level of alkaline phosphatase activity in growth plate increases as the chondrocytes mature and calcify their matrix, we have used this enzyme as a marker for chondrocyte differentiation (Wuthier and Register, 1985; O'Keefe et al. , 1989; Boyan et al. , 1992). This observation was validated in the culture model used in the present studies (Boyan et al. , 1988b). In culture, alkaline phosphatase activity increases as the cells re-express their in vivo phenotype, typical of their zone of origin within the growth plate. In post-confluent cultures, alkaline phosphatase continues to increase as the chondrocytes form multilamellar nodules (Schwartz et al. , 1995b). The activity of this enzyme is also regulated in a cell maturation-dependent manner (Schwartz and Boyan, 1988) by hormones known to regulate mineralization.

Alkaline phosphatase (EC 3. 1. 3. 1) specific activity was determined on both the cell layers (cells plus matrix vesicles), prepared as described below, or isolated cells (cells only), prepared as described above for the cell number studies. This enables one to infer the contribution of matrix vesicles to any change in alkaline phosphatase that might occur. Protein content of the wells was determined using commercially available kits (Micro BCA and Macro BCA Protein Assays, Pierce, Rockford, Ill.). Alkaline phosphatase activity was assessed by the release of p-nitrophenol from p-nitrophenylphosphate at pH 10. 25 (Bretaudiere and Spillman, 1984). Specific activity was obtained by normalization of the alkaline phosphatase activity to the amount of protein in the sample.

Cell layers were prepared by the method of Hale et al. (Hale et al., 1986). At harvest, the cells were washed twice with PBS and removed with a cell scraper. The cells were then centrifuged at 500×g for ten minutes. The supernatant was decanted, the pellet resuspended in PBS, and centrifuged again. Following the second spin, the supernatant was decanted and the pellet resuspended in 0.05% Triton X-100. Isolated cells were obtained via trypsinization, as described above, and resuspended in 0.05% Triton X-100. Enzyme assays were performed on the cell lysates that had been frozen and thawed three times.

[$^{35}$S]-Sulfate Incorporation

Proteoglycan synthesis was assessed by [$^{35}$S]-sulfate incorporation according to the method of O'Keefe et al. (O'Keefe et al., 1988). Four hours prior to harvest, [$^{35}$S]-sulfate (New England Nuclear, Boston, Mass.) was added to the media to a final concentration of 9 $\mu$Ci/ml. At harvest, the wells were washed with 500 $\mu$l PBS, the cell matrix collected in two 0.25ml portions in 0.25 M NaOH, and protein content determined using commercially available kits (BCA Protein Assays, Pierce, Rockford, Ill.). In order to determine the extent of [$^{35}$S]-sulfate incorporation, the sample volume was adjusted to 0.7 ml by the addition of 0.15 M NaCl. Samples were then transferred into dialysis tubing with a 12,000–14,000 molecular weight cut-off and dialyzed at 4° C. against a buffer containing 0.15 M NaCl, 20 mM $Na_2SO_4$, and 20 mM $Na_2HPO_4$ at pH 7.4. The dialysis solution was changed daily until the radioactivity in the dialysate reached background levels and the amount of [$^{35}$S]-sulfate incorporated into the cell layer determined using a liquid scintillation counter.

[$^3$H]-Proline Incorporation

Matrix protein synthesis was assessed by examining the extent of [$^3$H]-proline incorporation into collagenase-digestible protein (CDP) and noncollagenase-digestible protein (NCP) by the method of Peterkofsky and Diegelmann (Peterkofsky et al., 1971). At confluence, DMEM containing 10% FBS, vitamin C, antibiotics, 50 mg/ml $\beta$-amino proprionitrile (Sigma, St. Louis, Mo.) and 5 $\mu$Ci/ml L-[G-$^3$H]-proline (New England Nuclear, Boston, Mass.), in addition to PDGF-BB, were added to the wells.

The media and cell matrix were retrieved separately at harvest. The cell matrix was collected in two 0.2 ml portions of 0.2 M NaOH and proteins in both the media and matrix fractions precipitated with 0.1 ml 100% TCA containing 10% tannic acid and washed with 0.5 ml 10% TCA containing 1% tannic acid. After the initial wash, the two fractions were combined. The combined fractions were washed twice with 0.5 ml 10% TCA containing 1% tannic acid and then twice with 1ml ice-cold acetone. The final pellets were dissolved in 0.5 ml 0.05 M NaOH and protein content determined using commercially available kits (Micro BCA and BCA Protein Assays, Pierce, Rockford, Ill.).

Collagenase-digestible protein was separated from noncollagenase-digestible protein via a four-hour digestion of the pellet at 37° C. with 50 units/ml highly purified clostridial collagenase (Calbiochem, San Diego, Calif.) in a 0.032 N HCl solution containing 60 mM HEPES (N-2-hydroxyethyl piperazine-NO-2 ethane sulfonic acid), 1.25 mM N-ethyl maleimide, and 0.25 mM $CaCl_2$. Digestion of the pellet was terminated by the addition of 0.5 ml 10% TCA containing 0.5 % tannic acid at 0° C. Samples were then centrifuged for five minutes at 400×g at 4° C., the pellet resuspended in 0.5 ml 5 % TCA containing 0.25 % tannic acid, allowed to sit overnight at 4° C., centrifuged again, and resuspended in 0.5 ml 5 % TCA containing 0.25 % tannic acid. The supernatants from both spins were retained as the CDP fraction of the sample. The final suspended solution represented the NCP fraction of the sample. Counts in each fraction were determined using a liquid scintillation counter.

NCP synthesis was calculated after multiplying the labeled protein in NCP by 5.4 to correct for its relative abundance in collagen (Raisz et al., 1979). Percent collagen production was calculated by comparing CDP production with total CDP-plus-NCP production [CDP/(CDP)+NCP) *100].

Effect of PDGF-BB on Resting Zone Chondrocyte Differentiation

To determine whether PDGF-BB could induce a change in maturation state, we took advantage of the differential responsiveness of resting zone and growth zone chondrocytes to vitamin D metabolites. When resting zone cells are incubated with $10^{-7}$M 24,25-$(OH)_2D_3$, cell proliferation is not affected (Schwartz et al., 1989); alkaline phosphatase-specific activity is stimulated (Boyan et al., 1988a), whereas phospholipase $A_2$-specific activity in inhibited (Schwartz and Boyan, 1988); [$^{35}$S]-sulfate incorporation is increased (Schwartz et al., 1995a); and CDP is inhibited, NCP is not affected, and percent collagen production is inhibited (Schwartz et al., 1989). 1,25 -$(OH)_2D_3$ inhibits cell proliferation (Schwartz et al., 1989); has no effect on alkaline phosphatase or phospholipase $A_2$ (Schwartz and Boyan, 1988); inhibits CDP, has no effect on NCP, and inhibits percent collagen production. In contrast, growth zone chondrocytes respond to 1,25-$(OH)_2D_3$, with inhibition of cell proliferation (Schwartz et al., 1989); increased alkaline phosphatase and phospholipase $A_2$ (Schwartz and Boyan, 1988); increased CDP, no effect on NCP, and increased percent collagen production (Schwartz et al., 1989).

For these studies, confluent fourth passage resting zone chondrocyte cultures were incubated with 37.5 or 150 ng/ml PDGF-BB for 24, 48, 72 or 120 hours. At the end of each of these times, the media were replaced with experimental media containing $10^{-8}$ M $\alpha$25-$(OH)_2D_3$ and the cultures incubated for an additional 24 hours. At harvest, the cultures were analyzed as described above.

Statistical Analysis

Experiments were conducted at least twice and found to yield reproducible results. The data shown are from one representative experiment. Values given are mean ±standard error of the mean (SEM) of six individual cultures. Data were initially analyzed by analysis of variance (ANOVA) and, if differences existed, Student's t-tests for multiple comparisons using Bonferroni's correction were used. Differences were considered significant if $p<0.05$.

Results

Proliferation

Figure 2:
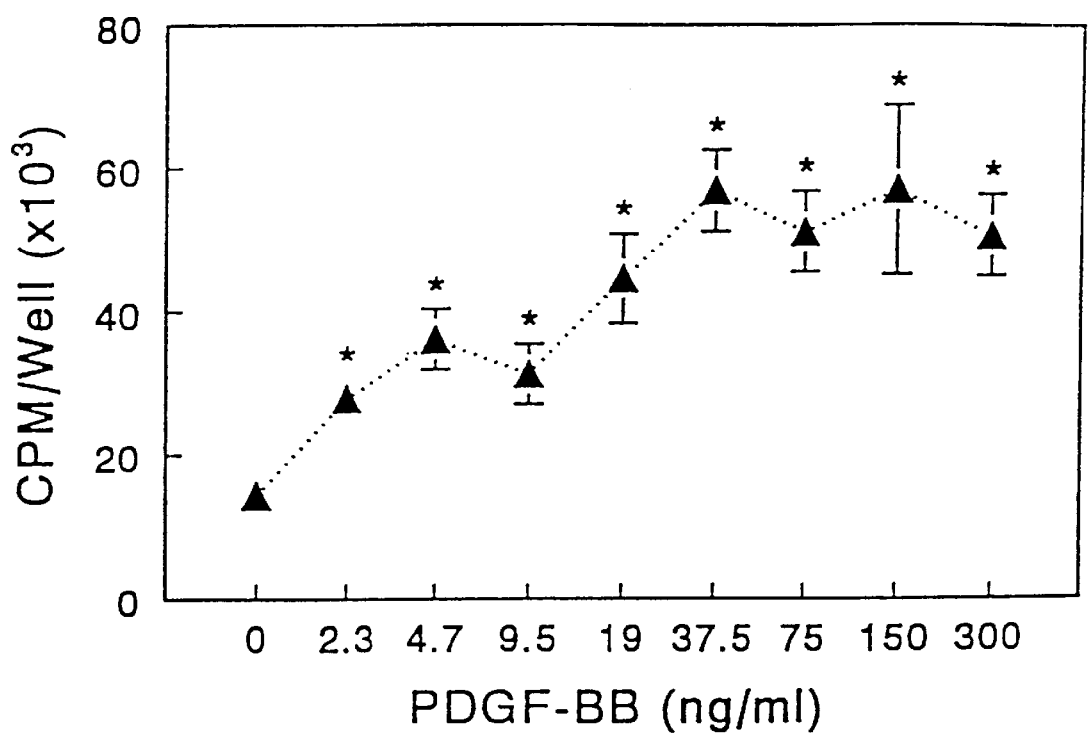
FIG. 2. [$^3$H]-Thymidine incorporation by resting zone chondrocytes after 24 hours of treatment with 0–300 ng/ml PDGF-BB. Subconfluent cells were made quiescent by reducing the serum concentration to 1% for 48 hours. At that time, the media were changed, Experimental media consisted of PDGF-BB in DMEM containing 1% FBS. Values are the mean ±SEM of six cultures. *P<0. 05, treatment vs. control. Data are from one of two replicate experiments yielding similar results.

Cultures stimulated for 24 hours with concentrations of PDGF-BB ranging from 4.7–300 ng/ml had significantly greater cell numbers than their controls (FIG. 1). The relationship between increasing dose and cell number was biphasic, peaking at 75 ng/ml. The results of the addition of PDGF-BB on DNA synthesis, as assessed by [$^3$H]-thymidine incorporation (FIG. 2), showed significantly greater stimulation of thymidine incorporation at all concentrations examined over controls. This increase appeared to be dose-dependent from 2.3–37.5 ng/ml, with the effects plateauing at concentrations above 37.5 ng/ml.

Figure 3:
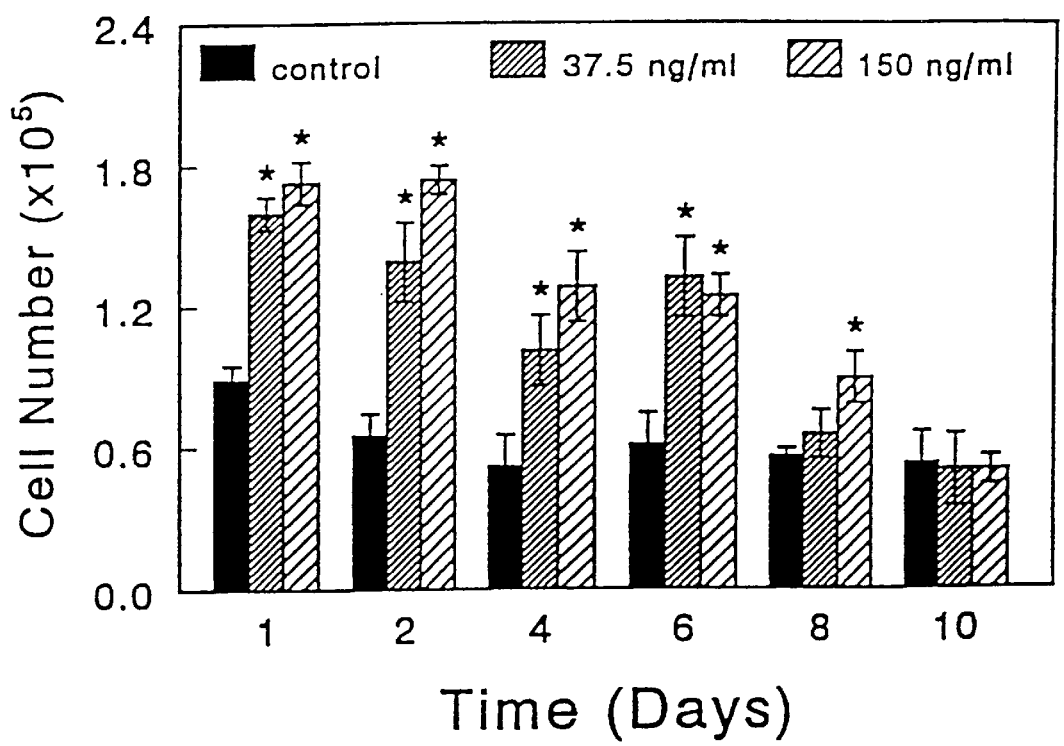
FIG. 3. Number of resting zone chondrocytes after treating confluent cultures with 0, 37. 5, or 150 ng/ml PDGF-BB for 1 to 10 days, Values are the mean ±SEM of six cultures. *P<0. 05, treatment vs. control. Data are from one of two replicate experiments yielding similar results.

Prolonged exposure to PDGF for one to eight days resulted in a significant increase in cell number (FIG. 3). The observed effect was time-dependent, decreasing with time of exposure to the growth factor. In addition, the effect appeared to be dose-dependent since at the first four time points cultures treated with either 37. 5 or 150 ng/ml contained significantly more cells than did untreated controls. However, the difference between cultures treated with 37. 5 or 150 ng/ml was not statistically significant at any of the time points examined.

Alkaline Phosphatase Specific Activity

Figure 4:
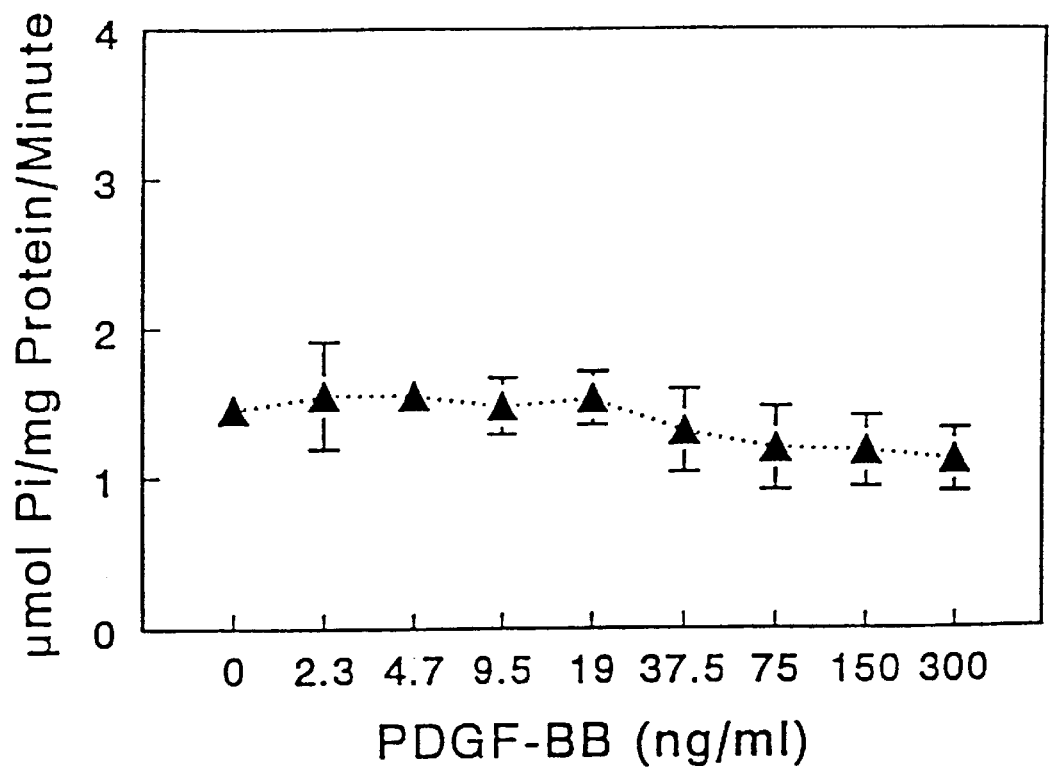
FIG. 4. Alkaline phosphatase specific activity of resting zone chondrocyte cell layers after treatment of confluent cultures with 0–300 ng/ml PDGF-BB for 24 hours. Values are the mean ±SEM of six cultures. Data are from one of two replicate experiments yielding similar results.

There was no evidence of PDGF affecting chondrocyte alkaline phosphatase specific activity after 24 hours of treatment (FIG. 4). The enzyme activity of the cell layer, which includes the extracellular matrix and its incorporated matrix vesicles, was not different from that of the controls at any of the various concentrations examined. Similarly, treatment with PDGF for 24 hours had no effect on alkaline phosphatase specific activity of cells isolated by the matrix by trypsinization (data not shown).

Figure 5:
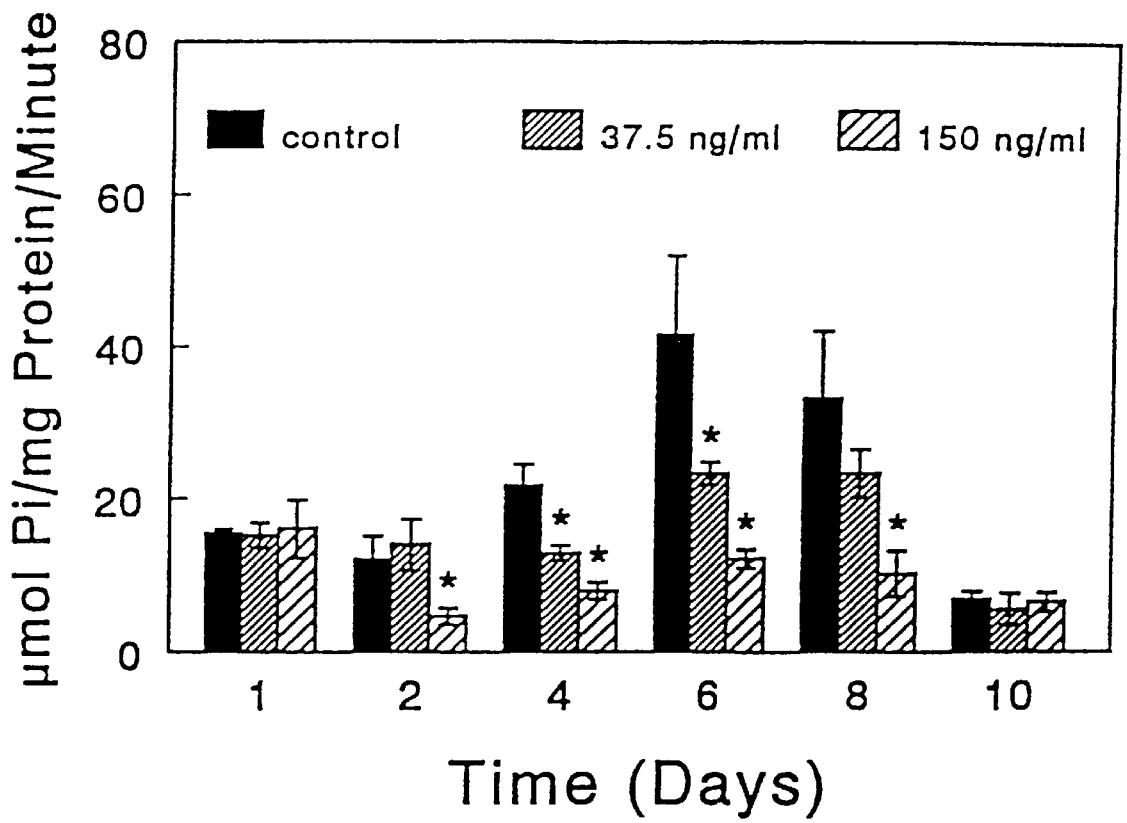
FIG. 5. Alkaline phosphatase specific activity of resting zone chondrocytes isolated from confluent cultures treated with 0, 37. 5, or 150 ng/ml PDGF-BB for 1 to 10 days. Values are the mean ±SEM of six cultures. *P<0. 05, treatment vs. control. Data are from one of two replicate experiments yielding similar results.
Figure 6:
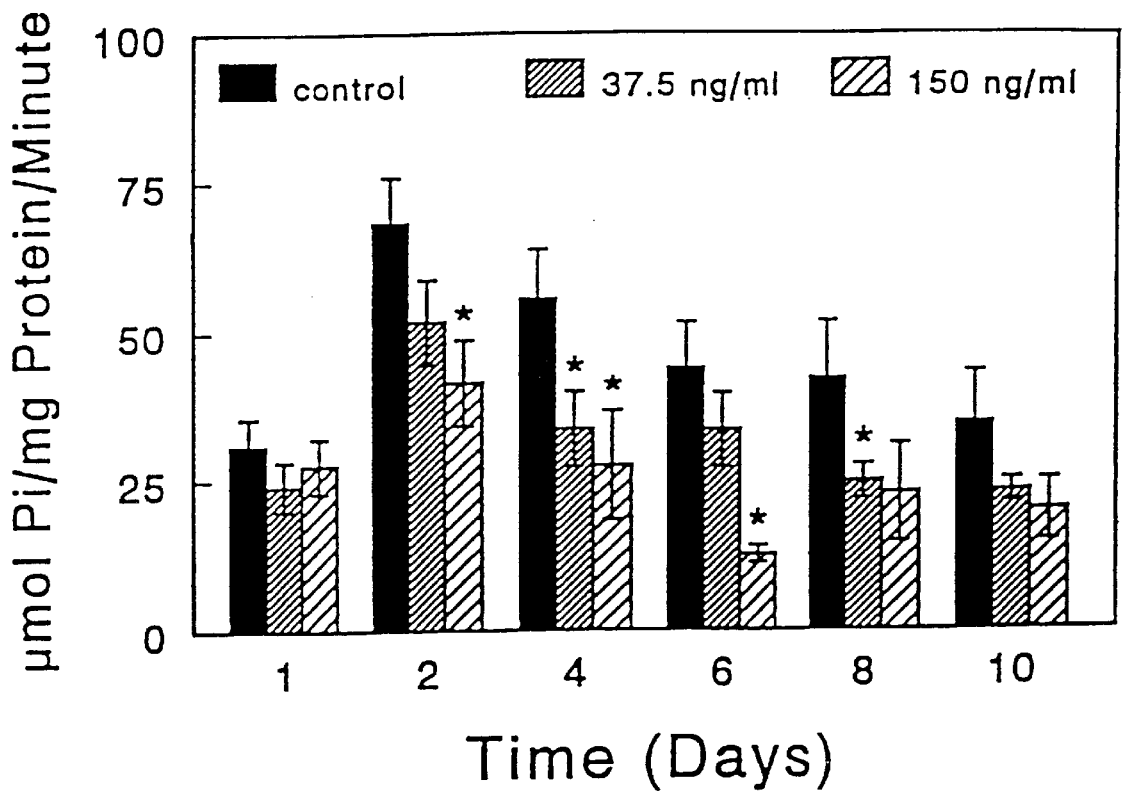
FIG. 6. Alkaline phosphatase specific activity in resting zone chondrocyte cell layers after treatment of confluent cultures with 0, 37. 5, or 150 ng/ml PDGF-BB for 1 to 10 days. Values are the mean ±SEM of six cultures. *$P<0.05$, treatment vs. control. Data are from one of two replicate experiments yielding similar results.
Figure 7:
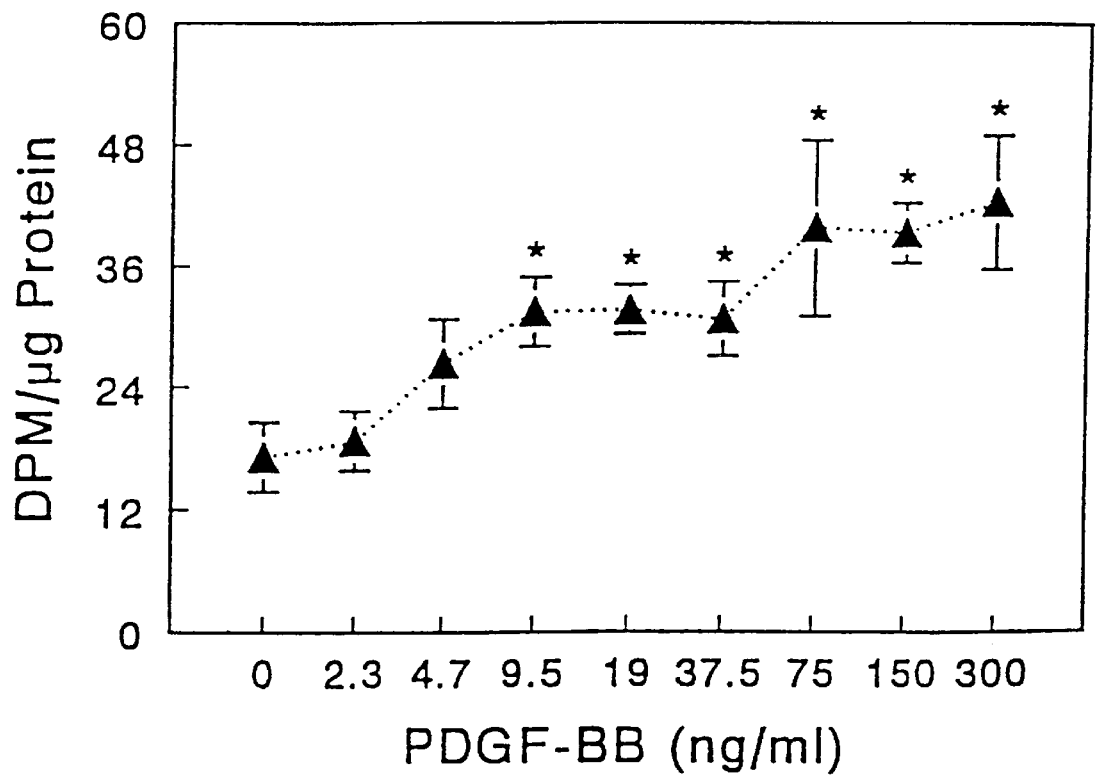
FIG. 7. [$^{35}$S]-Sulfate incorporation by confluent cultures of resting zone chondrocytes after treatment with 0–300 ng/ml PDGF-BB for 24 hours. Values are the mean ±SEM of six cultures. *$P<0.05$, treatment vs. control. Data are from one of two replicate experiments yielding similar results.
Figure 8:
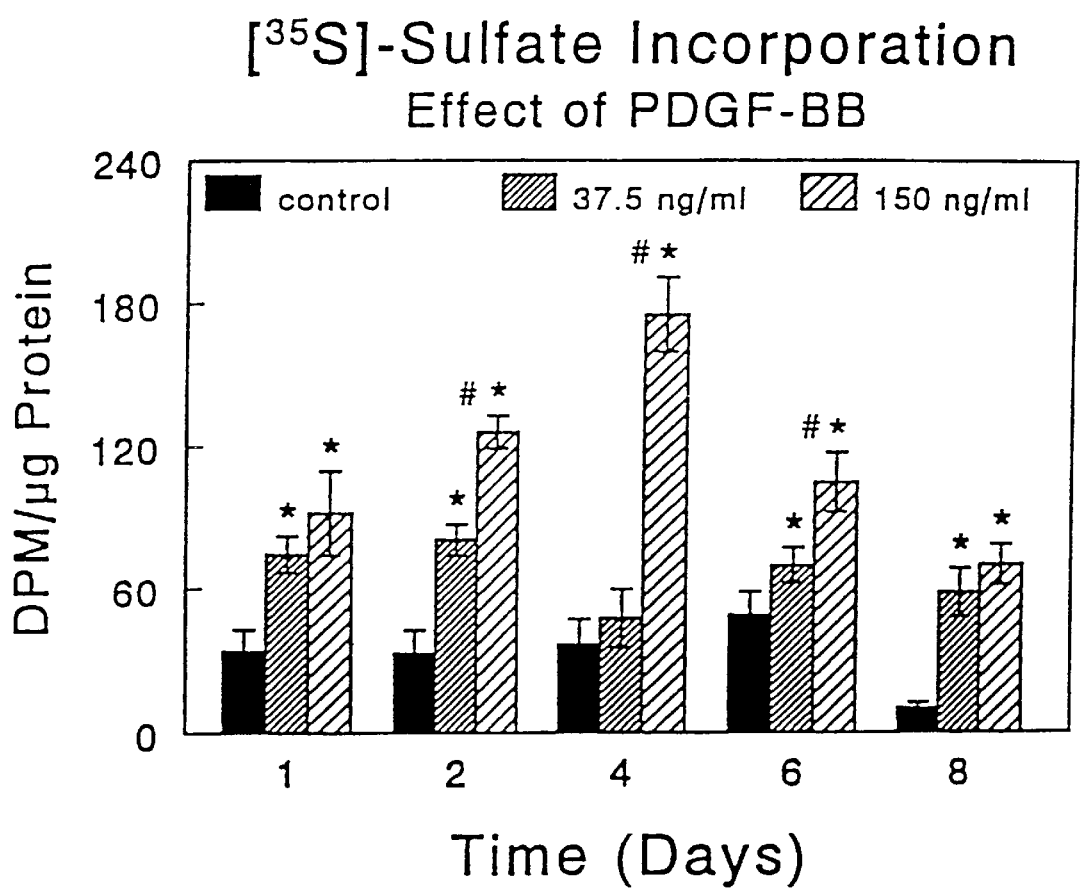
FIG. 8. [$^{35}$S]-Sulfate incorporation by confluent cultures of resting zone chondrocytes after treatment with 0, 37. 5, or 150 ng/ml PDGF-BB for 1 to 8 days. Values are the mean ±SEM of six cultures. *$P<0.05$, treatment vs. control; #$P<0.05$, 37,5 vs. 150 ng/ml. Data are from one of two replicate experiments yielding similar results.

Prolonged exposure to PDGF, however, inhibited both isolated cell and cell layer alkaline phosphatase specific activity (FIGS. 5 and 6). Significant decreases in cell alkaline phosphatase were noted after cultures were exposed to 150 ng/ml PDGF-BB for two to eight days (FIG. 5). The inhibitory effects, although less profound, were also noted at days 4 an 6 in cells isolated from cultures exposed to 37. 5 ng/ml cytokine (FIG. 5). Cell layer alkaline phosphatase-specific activity appeared to be less sensitive to inhibition by PDGF-BB. Although 37. 5 ng/ml caused a decrease in enzyme activity in the cell layer, these slightly lower levels were not significantly different from those of the controls at any time point (FIG. 6). Treatment with 150 ng/ml for two to six days, however, produced a significant decrease in cell layer alkaline phosphatase specific activity. [$^{35}$S]-Sulfate Incorporation PDGF-BB caused a dose-dependent stimulation of proteoglycan production, as indicated by [$^{35}$S]-sulfate incorporation. Proteoglycan production by resting zone cells was 2. 5–3. 5 times that of controls (FIG. 7). Dose-dependent increases in proteoglycan production were also noted in cultures treated with PDGF-BB for prolonged time periods (FIG. 8). Production was significantly greater than controls for both concentrations examined at all times examined, peaking at day 4 with treatment. Cultures stimulated with 150 ng/ml generally had greater levels of [$^{35}$S]-sulfate incorporation than did those treated with 37. 5 ng/ml. Differences between these two concentrations, however, were only significant at 2, 4 and 6 days.

[$^3$H]-Proline Incorporation

Figure 9:
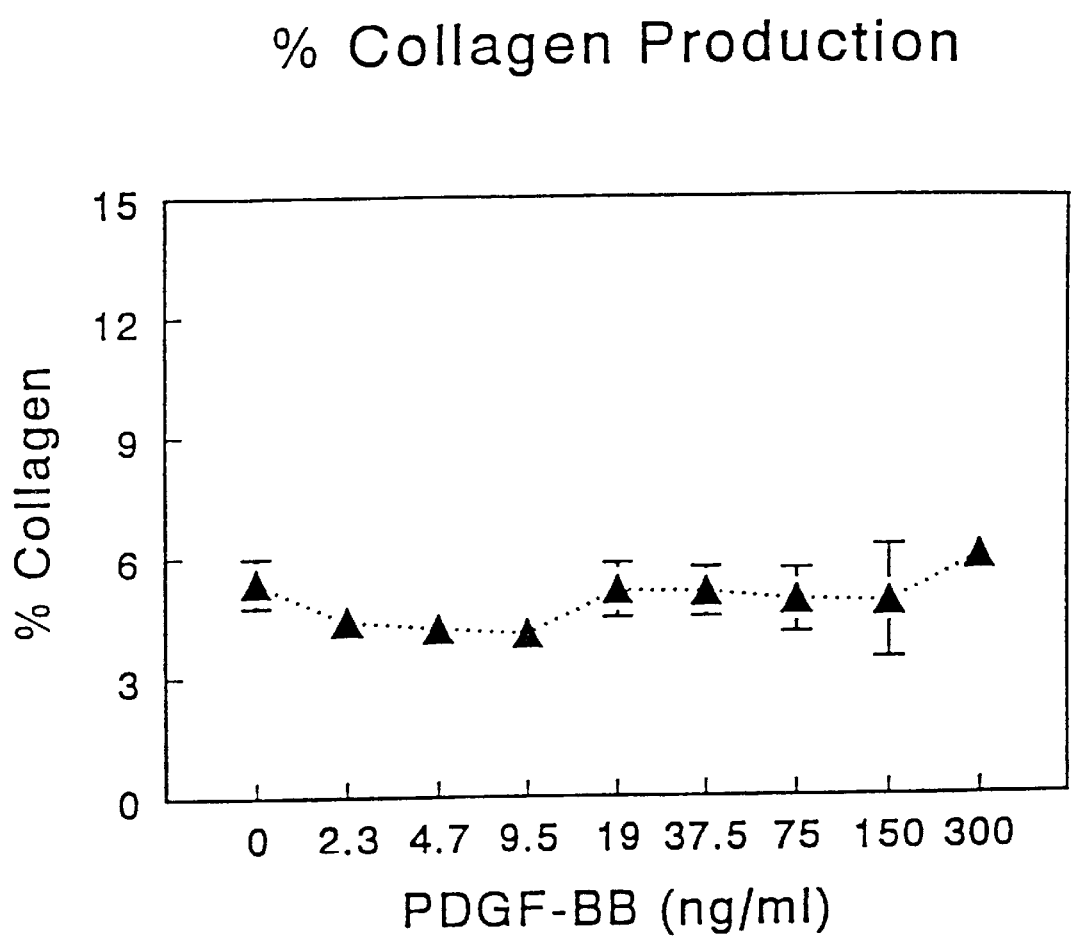
FIG. 9. Percent collagen production by confluent resting zone chondrocytes after 24 hours of treatment with 0–300 ng/ml PDGF-BB. Values are the mean ±SEM of six cultures. Data are from one of two replicate experiments yielding similar results.

The addition of PDGF-BB to resting zone cultures for 24 hours did not alter the amount of either collagenase-digestible or noncollagenase-digestible protein production. Similarly, percent collagen production by cells treated with PDGF-BB was not significantly different from controls (FIG. 9). Further, no effect of PDGF-BB between 1 and 8 days was observed.

Effect of PDGF-BB on Resting Zone Chondrocyte Differentiation

Figure 10:
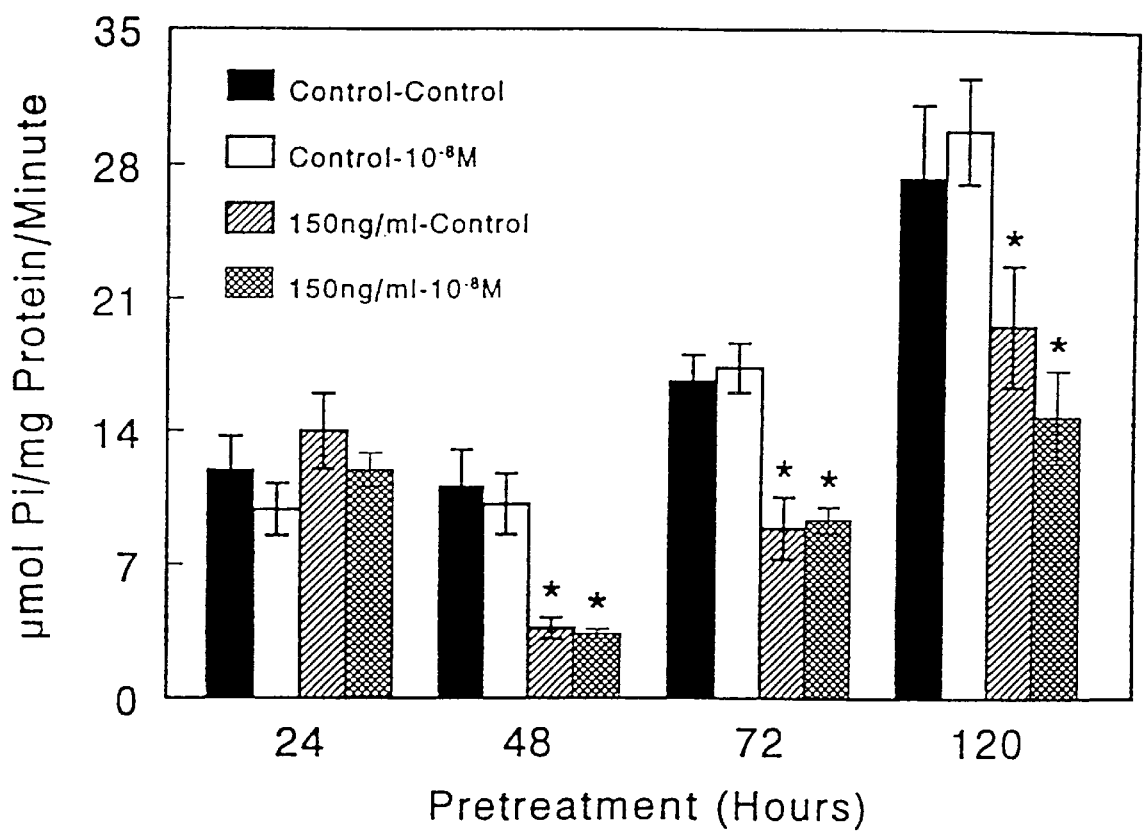
FIG. 10. Alkaline phosphatase specific activity of resting zone chondrocytes after treatment with vehicle (control) or PDGF-BB (150 ng/ml) for 24–120 hours. At the end of treatment with vehicle or PDGF-BB, the media were removed and fresh media containing vitamin D vehicle (control) or 1,25-(OH)$_2$D$_3$ ($10^{-8}$M) added. The cultures were then incubated for an additional 24 hours and the cell layers assayed for alkaline phosphatase specific activity. Values are the mean ±SEM of six cultures. *$P<0.05$, vs. control-control or control-$10^{-8}$M 1,25-(OH)$_2$D$_3$. Data are from one of two replicate experiments yielding similar results.

Treatment of confluent cultures of resting zone cells with PDGF-BB for 24, 48, 72 or 120 hours did not result in a 1,25-(OH)$_2$D$_3$-responsive phenotype for any of the parameters tested. A typical example of the results obtained is shown in FIG. 10 for alkaline phosphatase activity. Alkaline phosphatase-specific activity was inhibited in cultures treated for 48, 72 and 120 hours with 150 ng/ml PDGF-BB. When either these cultures, or chondrocytes cultured in control media for comparable periods of time, were challenged with 1,25-(OH)$_2$D$_3$ for an additional 24, hours, no change in enzyme activity was noted.

This invention has been illustrated by the foregoing examples; however, as will be appreciated by those skilled in the art, various substitutions and modifications may be made based on the teachings herein and knowledge in the art. The invention is not limited to the specific embodiments exemplified, but is defined by the claims hereof.

We claim:

1. A method for resurfacing an articular cartilage defect in a patient comprising:

(a) isolating chondrocyte cells from the patient;

(b) contacting said cells with a Platelet-Derived Growth Factor (PDGF) selected from the group consisting of PDGF-BB, PDGF-AA and PDGF AB for about 30 minutes to about 24 hours in an amount effective to inhibit chondrocyte endochondral maturation to hypertrophic and in the substantial absence of growth factors which promote the hypertrophic stage of cell differentiation;

(c) loading said cells onto a cell scaffolding material; and (d) placing said cell scaffolding material in said defect.

2. The method of claim 1 wherein said scaffolding material is biodegradable.

* * * * *

UNITED STATES PATENT AND TRADEMARK OFFICE
CERTIFICATE OF CORRECTION

PATENT NO. : 6,001,352

DATED : December 14, 1999

INVENTOR(S) : Boyan et al.

It is certified that error appears in the above-identified patent and that said Letters Patent is hereby corrected as shown below:

At column 9, line 15, delete "1α,25" and replace with --1a,25--.

At column 12, line 40, delete "α 25" and replace with --1a,25--.

Signed and Sealed this

Fifth Day of September, 2000

Attest:

Attesting Officer

Q. TODD DICKINSON
Director of Patents and Trademarks

UNITED STATES PATENT AND TRADEMARK OFFICE
CERTIFICATE OF CORRECTION

PATENT NO. : 6,001,352
DATED : December 14, 1999
INVENTOR(S) : Barbara D. Boyan, et al It is certified that error appears in the above-identified patent and that said Letters Patent is hereby corrected as shown below:

On title page, item [73], should read
--Board of Regents, University of Texas System,
Austin, Texas--

Signed and Sealed this

Twenty-fourth Day of October, 2000

Attest:

Q. TODD DICKINSON

*Attesting Officer*     *Director of Patents and Trademarks*